United States Patent
Müller et al.

(10) Patent No.: US 6,271,374 B1
(45) Date of Patent: *Aug. 7, 2001

(54) STABLE CRYSTALLINE (6S)- AND (6R)-TETRAHYDROFOLIC ACID

(75) Inventors: Hans Rudolf Müller, Schaffhausen; Martin Ulmann, Dachsen; Rudolf Moser, Schaffhausen; Thomas Ammann, Marthalen, all of (CH)

(73) Assignee: Eprova AG, Schaffhausen (CH)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/013,266

(22) Filed: Jan. 26, 1998

Related U.S. Application Data

(63) Continuation of application No. 08/437,716, filed on May 9, 1993, now abandoned.

(30) Foreign Application Priority Data

May 9, 1994 (CH) .......................................... 01 442/94-6

(51) Int. Cl.$^7$ ................................................. C07D 475/04
(52) U.S. Cl. ............................................................. 544/258
(58) Field of Search .............................................. 544/258

(56) References Cited

U.S. PATENT DOCUMENTS

| 5,006,655 | 4/1991 | Müller et al. ........................ 544/528 |
| 5,324,836 | * 6/1994 | Muller et al. ........................ 544/258 |
| 5,489,684 | * 2/1996 | Jequier et al. ....................... 544/258 |

FOREIGN PATENT DOCUMENTS

| 2323124 | 11/1973 | (DE) . |
| 0495204 | 7/1992 | (EP) . |
| 0600460 | 6/1994 | (EP) . |
| 88/08844 | 11/1988 | (WO) . |

OTHER PUBLICATIONS

Rees, et al. Tetrahedron vol. 42 pp 117–136, 1986.*
Daus, Intellectual Property Journal, vol. 12, No. 3, Sep. 1998 pp. 333–354 Carswell Aullistr.*
Cram and Hammond, "Organic Chemistry" Seed Ed 1964, McGraw Hill Book Co.*

* cited by examiner

Primary Examiner—John M. Ford
(74) Attorney, Agent, or Firm—Millen, White, Zelano & Branigan, P.C.

(57) ABSTRACT

Pure and extremely stable crystalline (6S)- and (6R)-tetrahydrofolic acids, absolutely inert even when exposed to air and elevated temperature without stabilizers being added, are prepared by a crystallization process at a pH of ≧3.5 for the preparation of crystalline (6S)-tetrahydrofolic acid and at a pH of ≧2 for the preparation of crystalline (6R)-tetrahydrofolic acid.

17 Claims, No Drawings

STABLE CRYSTALLINE (6S)- AND (6R)-TETRAHYDROFOLIC ACID

This application is a continuation of application of Ser. No. 08/437,716, filed May 9, 1995, now abandoned, for which a priority date of May 9, 1994 is claimed through Swiss application no. 01442/94-6.

BACKGROUND OF THE INVENTION

This invention relates to crystalline N-[4-[[(2-amino-1,4,5,6,7,8-hexahydro-4-oxo-(6S)- and -(6R)-pteridinyl)methyl]amino]benzoyl]-L-glutamic acid (termed crystalline (6S)- or (6R)-tetrahydrofolic acid herein-below), to its use, and to a process for its preparation.

Tetrahydrofolic acid derivatives have 2 asymmetric centres. Since these derivatives are synthesized from folic acid, i.e. N-(pteroyl)-L-glutamic acid, the optically active C atom in the glutamic acid moiety is in the L form, while the optically active C atom in the 6-position, which is usually formed by hydrogenation of the double bond in the 5,6-position of the pteroyl radical, exists in the racemic, i.e. (6R,S) form. Accordingly, synthetic tetrahydrofolic acid derivatives are composed of a 1:1 mixture of 2 diastereomers.

Tetrahydrofolates are mainly used in the form of calcium 5-formyl-5,6,7,8-tetrahydrofolate (leucovorin) or calcium 5-methyl-5,6,7,8-tetrahydrofolate as pharmaceuticals for the treatment of megaloblastic folic acid anaemia, as an antidote for improving the tolerance of folic acid antagonists, specifically aminopterin and methotrexate in cancer therapy ("antifolate rescue"), for enhancing the therapeutic effect of fluorinated pyrimidines and for the treatment of autoimmune diseases such as psoriasis and rheumatic arthritis, for improving the tolerance of certain antiparasitics, such as trimethoprim-sulfamethoxazole, and for reducing the toxicity of dideazatetrahydrofolates in chemotherapy. Tetrahydrofolic acid is also used as starting material for the preparation of a variety of tetrahydrofolic acid derivatives.

To date, the direct use of tetrahydrofolic acid as a pharmaceutical and as a starting material for the preparation of a variety of tetrahydrofolic acid derivatives was made impossible for all practical purposes by the difficulty encountered when preparing tetrahydrofolic acid in a purity which is acceptable for a pharmaceutical active substance and by the extreme instability of tetrahydrofolic acid, in particular its pronounced sensitivity to oxidation [see, in this context, also A. L. Fitzhugh, Pteridines 4(4), 187–191 (1993)]. Various methods were developed to overcome this instability, and particular mention must be made in connection with the present invention of DE-OS 2 323 124. Specific mention must also be made of EP 600 460 corresponding to U.S. Pat. No. 5,489,684 in the context of processes for the preparation of tetrahydrofolic acid an in connection with the present invention. However, no process which is feasible on an industrial scale has been found to date for the preparation of ultrapure, sufficiently stable tetrahydrofolic acid which would allow the pharmaceutical application of tetrahydrofolic acid.

SUMMARY OF THE INVENTION

Surprisingly, it has been found that chemically and optically ultrapure (6S) or (6R) tetrahydrofolic acid with an outstanding stability can be obtained by crystallizing optically pure (6S)- or optically pure (6R)-, enriched (6S)- or enriched (6R)- or else (6R,S)-tetrahydroiolic acid. The resulting crystalline (6S)- and/or (6R)- tetrahydrofolic acid allows for the first time the use of the substance as a pharmaceutical or as a starting material for the industrial-scale preparation of other ultrapure tetrahydrofolic acid derivatives.

(6S)-tetrahydrofolic acid is crystallized from a polar medium at a pH of $\geq 3.5$, while (6R)-tetrahydrofolic acid is crystallized from a polar medium at a pH of $\geq 2$.

Suitable polar media include but are not limited to: especially water or a mixture of water and an organic solvent which is miscible with water, such as water-soluble alcohols, for example methanol, ethanol, n-propanol, iso-propanol, ethylene glycol, a water-soluble lower aliphatic carboxylic acid, for example formic acid, acetic acid, lactic acid, or water-soluble amides, for example formamide, dimethylformamide, dimethylacetamide, 1-methylpyrrolidone, 2-methylpyrrolidone, 2-piperidinone. No particular restrictions apply to the nature of the solvent employed and the mixing ratio, since crystalline (6S)-tetrahydrofolic acid and crystalline (6R)-tetrahydrofolic acid in general have lower solubility characteristics than the corresponding amorphous forms.

To initiate crystallization of (6S)-tetrahydrofolic acid, a pH of between 3.5 and 6.5 is particularly suitable. To initiate crystallization of (6R)-tetrahydrofolic acid, a pH of between 2 and 5.5 is particularly suitable. The optimum pH for initiating crystallization depends on the materials employed and the intended object and can be determined by simple experiments. In general, a higher salt content in the starting solution will require a lower pH for initiating crystallization, and a lower pH for initiating crystallization requires a slower crystallization process since otherwise amorphous tetrahydrofolic acid precipitates at a pH of around 3. For example, direct crystallization of (6S)-tetrahydrofolic acid from a reaction solution obtained by reducing folic acid using borohydride strictly requires a pH of $\leq 4.8$ for initiating crystallization. After crystallization has been initiated, the pH may be varied.

During the crystallization of (6S)-tetra-hydrofolic acid and also during the crystallization of (6R)-tetrahydrofolic acid, the pH rises or may be kept constant by adding an acid or buffer. In the case of the crystallization of (6S)-tetrahydrofolic acid, a pH of between 4.5 and 5.5 during the crystallization is preferred if it is intended to optically enrich (6S) tetrahydrofolic acid, while a pH of between 3.5 and 4.5 during the crystallization is preferred if it is intended to prepare stable crystalline (6S)-tetrahydrofolic acid. In the case of the crystallization of (6R)-tetrahydrofolic acid, a pH of between 3.5 and 4.5 during the crystallization is preferred independently of the desired result. The crystallization can be carried out in each case at room temperature, at elevated temperature or else at reduced temperature.

The time required for crystallization varies between a few minutes and several days. As a rule, longer crystallization times result in higher purity and more stable products.

(6S)- and (6R)-tetrahydrofolic acid crystallize spontaneously by slowly adjusting the pH, either starting from a pH which is lower than the pH suitable for initiating the crystallization of the isomer in question, or, preferably, starting from a higher pH. Crystallization may be triggered by seeding with the corresponding crystalline tetrahydrofolic acid in the pH range which is suitable for initiating crystallization of the isomer in question.

The starting material for the crystallization can be racemic (6R,S)-tetrahydrofolic acid, enriched (6S)- or (6R)-tetrahydrofolic acid as well as amorphous or crystalline (6S)- or (6R)-tetrahydrofolic acid. Suitable as starting material are not only isolated solid substances, such as, for example, (6R,S)-tetrahydrofolic acid, addition salts of sulphuric and sulphonic acid with (6S)-tetrahydrofolic acid prepared as described in EP 495 204, corresponding to U.S. Pat. No. 5,324,836 as well as tetrahydrofolic acid which has been prepared in situ from folic acid by catalytic hydrogenation or by reduction using boron hydride. (6R) tetrahydrofolic acid may be crystallized directly from the (6S)-tetrahydrofolic acid crystallization mother liquor. Both isomers may be crystallized either from a solution obtained, for example by bringing the pH to >7 or <2, or from a suspension.

By using amorphous or partially crystalline optically pure tetrahydrofolic acid or salts thereof as the starting material for the crystallization, the above described process yields crystalline tetrahydrofolic acid of previously unachieved purity (>98%) and, equally, previously unachieved stability.

The invention also relates to the use of crystalline (6S)- and/or (6R)-tetrahydrofolic acid as a component for the preparation of pharmaceuticals or for the preparation of other tetrahydrofolic acid derivatives since the quality of crystalline (6S)- and (6R)-tetrahydrofolic acid in solid form remains high over a virtually unlimited period due to its outstanding stability. The invention also relates to pharmaceutical preparations comprising crystalline (6S)- and/or (6R)-tetrahydrofolic acid. The pharmaceutical preparation is made by known processes, such as, for example, lyophilization. The uses and methods of use are analogous to those of known substances from the field of the tetrahydrofolates, such as, for example, 5-formyl-5,6,7,8-tetrahydrofolic acid.

The invention furthermore relates to a process for separating (6R,S)-tetrahydrofolic acid by fractional crystallization to give the two diastereomers (6S)- and (6R)-tetrahydrofolic acid. This process is very simple and high-yielding. Even upon the first crystallization of a crude racemic (6R,S)-tetrahydrofolic acid, crystalline (6S)-tetrahydrofolic acid is obtained in yields of above 70% while its (6S) component amounts to above 75%, and crystalline (6R)-tetrahydrofolic acid is obtained in yields of above 50% while its (6R) component amounts to above 80%. Further crystallization steps under analogous conditions allow crystalline (6S)- and (6R)-tetrahydro-folic acid with an isomeric purity of above 95% to be obtained.

(6R)- or (6S)-tetrahydrofolic acid can also be used directly without isolation for the preparation of other tetrahydrofolic acid derivatives. For example, enriched 5,10-methylene-(6S)-tetrahydrofolic acid can be prepared very easily by adding formaldehyde to a (6R)-tetrahydrofolic acid solution.

Without further elaboration, it is believed that one skilled in the art can, using the preceding description, utilize the present invention to its fullest extent. The following preferred specific embodiments are, therefore, to be construed as merely illustrative, and not limitative of the remainder of the disclosure in any way whatsoever.

In the foregoing and in the following examples, all temperatures are set forth uncorrected in degrees Celsius and unless otherwise indicated, all parts and percentages are by weight.

The entire disclosures of all applications, patents and publications, cited above and below, and of corresponding Swiss application 01442/94-6, are hereby incorporated by reference.

The tetrahydrofolic acid contents and the isomer contents given in the following examples were in each case determined by HPLC. All tetrahydrofolic acid contents are based on the anhydrous substance.

EXAMPLE 1

(Stabilities)

To determine the stability of crystalline (6S)- and (6R)-tetrahydrofolic acid, the substances together with comparison samples were stored under severe conditions at 60° C. in the air. The remaining tetrahydrofolic acid content was measured at periodic intervals and is shown in comparison with the initial value.

|  | Test period in days at 60° C. in air | | | | | | | |
| --- | --- | --- | --- | --- | --- | --- | --- | --- |
|  | 0 | 2 | 6 | 13 | 21 | 28 | 57 | 360 |
| Crystalline (6S)-tetrahydrofolic acid | 100.0% | 100.1% | 102.5% | 98.7% | 103.6% | 103.1% | 101.2% | 93.3% |
| Crystalline (6R)-tetrahydrofolic acid | 100.0% | 98.4% | 96.1% | 93.3% | 92.7% |  | 82.0% |  |
| "Yamanouchi's crystalline (6R,S)-tetrahydrofolic acid" | 100.0% | 83.6% |  | 48.6% | 31.0% |  | 13.4% |  |
| Amorphous (6S)-tetrahydrofolic acid | 100.0% | 60.4% |  | 13.7 | 7.9% |  |  |  |
| amorphous (6R)-tetrahydrofolic acid | 100.0% | 70.5% |  | 29.1% | 21.6% |  | 9.8% |  |
| amorphous (6R, S)-tetrahydrofolic acid | 100.0% | 53.4% |  | 17.4% | 13.2% |  |  |  |

Even after a prolonged test period at 60° C. in the air, crystalline (6S)- and (6R)-tetrahydrofolic acid remain very pale, almost white. In contrast, the other products which are included for comparison reasons discolor rapidly to a high degree.

The substances employed for the stability tests were prepared as follows:

crystalline (6S)-tetrahydrofolic acid as in Example 6 of the present patent application crystalline (6R)-tetrahydrofolic acid as in Example 9 of the present patent application "Yamanouchi's crystalline (6R,S)-tetrahydrofolic acid" as in DE-OS 2 323 124, Example 3 amorphous (6S)-tetrahydrofolic acid (6S)-tetrahydrofolic acid is dissolved in acetic acid and precipitated using diethyl ether amorphous (6R)-tetrahydrofolic acid (6R)-tetrahydrofolic acid is dissolved in acetic acid and precipitated using diethyl ether amorphous (6R,S)-tetrahydrofolic acid (6R,S)-tetrahydrofolic acid is dissolved in acetic acid and precipitated using diethyl ether.

EXAMPLE 2
(Powder X-ray Diagrams)

To characterize the structural properties (crystallinity) of the crystalline (6S)- and (6R)-tetrahydrofolic acid, powder X-ray diagrams (diffraction spectra) were recorded of these substances together with comparison samples under identical conditions.

Crystalline (6S)- and crystalline (6R)-tetrahydrofolic acid both result in neatly resolved, differing spectra with sharp bands and a low degree of background. The spectra suggest high contents of crystalline matter. In contrast, "Yamanouchi's crystalline (6R,S)-tetrahydrofolic acid" results in a poorly resolved spectrum with fuzzy bands (diffuse maxima) and a high degree of background. This spectrum suggests predominantly amorphous (6R,S)-tetrahydrofolic acid and only a low percentage of crystalline matter.

Substances used for producing the powder X-ray diagrams were prepared as follows:
- crystalline (6S)-tetrahydrofolic acid as in Example 6 of the present patent application
- crystalline (6R)-tetrahydrofolic acid as in Example 9 of the present patent application
- "Yamanouchi's crystalline (6R,S)-tetrahydrofolic acid" as in DE-OS 2 323 124, Example 3

EXAMPLE 3 a) 4 g of (6R,S)-tetrahydrofolic acid are suspended in 16 ml of water and the pH is brought to 9 using 25% ammonia. At 50° C., the resulting solution is brought to pH 5 using hydrochloric acid and then slowly to the desired pH using sodium hydroxide solution. 2 ml aliquots are sampled at the pH indicated, filtered with suction and washed with a small amount of water.

| pH | Quantity | Percentage of (6S) |
|---|---|---|
| pH 5.5 | 0.03 g | 87.8% |
| pH 6.0 | 0.06 g | 87.8% |
| pH 6.4 | 0.02 g | 88.6% | b) 4 g of (6R,S)-tetrahydrofolic acid are suspended in 16 ml of water and brought to pH 9 using 25% ammonia. At 50° C., the resulting solution is brought to pH 5 using hydrochloric acid and then slowly to the desired pH using hydrochloric acid. 2 ml aliquots are sampled at the pH indicated, filtered with suction and washed with a small amount of water.

| pH | Quantity | Percentage of (6S) |
|---|---|---|
| pH 4.8 | 0.09 g | 72.7% |
| pH 4.5 | 0.15 g | 57.9% |
| pH 4.2 | 0.27 g | 51.8% | c) 4 g of (6R,S)-tetrahydrofolic acid are suspended in 16 ml of water and brought to pH 9 using 25% ammonia. At 50° C., the resulting solution is brought to pH 5 using hydrochloric acid and then slowly to the desired pH, again using hydrochloric acid. 2 ml aliquots are sampled at the pH indicated, filtered with suction and washed with a small amount of water.

| pH | Quantity | Percentage of (6S) |
|---|---|---|
| pH 4.1 | 0.16 g | 56.2% |
| pH 3.8 | 0.10 g | 52.2% |
| pH 3.5 | 0.22 g | 51.8% |
| pH 3.0 | 0.12 g | 51.6% | d) 10 g of (6R,S)-tetrahydrofolic acid are suspended in 80 ml of water and brought to pH 1.3 using 1N hydrochloric acid. At room temperature, the resulting solution is slowly brought to the desired pH using 1.8 N ammonia. 2 ml aliquots are sampled at the pH indicated, filtered with suction and washed with a small amount of water.

| pH | Quantity | Percentage of (6S) |
|---|---|---|
| pH 2.0 | 0.03 g | 50.3% |
| pH 2.3 | 0.13 g | 50.5% |
| pH 2.5 | 0.12 g | 49.3% |
| pH 2.8 | 0.22 g | 50.8% |
| pH 3.1 | 0.17 g | 49.5% |
| pH 3.5 | 0.21 g | 51.5% |
| pH 4.0 | 0.14 g | 59.1% |
| pH 4.5 | 0.16 g | 56.1% |
| pH 5.1 | 0.22 g | 72.7% |
| pH 5.5 | 0.20 g | 70.9% |

The process parameters of the data listed in Tables a) to d) are not optimal since all experiments were carried out following the same protocol to improve their comparability.

EXAMPLE 4

5 g aliquots of (6R,S)-tetrahydrofolic acid are suspended in 50 ml of water and allowed to stand for days at room temperature or at 40° C. After filtration with suction (filtration temperature=crystallisation temperature) and washing, the following results are obtained:

| | RT | | 40° C. | |
|---|---|---|---|---|
| | Quantity | percentage of (6S) | Quantity | Percentage of (6S) |
| pH 3.1[1] | 4.2 g | 52.5% | 4.5 g | 52.2% |
| pH 4.2[2] | 3.5 g | 58.9% | 3.9 g | 59.3% |
| pH 5.1[2] | 1.8 g | 82.1% | 1.5 g | 81.0% |

[1] pH when suspending (6R,S)-tetrahydrofolic acid with-out correcting agent,-in analogy to DE-OS 2 323 124, Example 3
[2] brought to the desired pH using sodium hydroxide solution.

The process parameters of the data listed in the table are not optimal since all experiments were carried out following the same protocol to improve their comparability.

EXAMPLE 5

40 g of (6R,S)-tetrahydrofolic acid are suspended in 160 ml of water and brought to pH 9.3 using 25% ammonia. At 50° C., the resulting solution is slowly brought to pH 5.1 using hydrochloric acid, and the pH is kept at between 5.1 and 5.2 during the following crystallization phase. When the crystallization has ended, the mixture is cooled to 0–5° C., filtered under pressure and washed with water.

This gives 19 g of crystalline (6S)-tetrahydrofolic acid with a chemical content of 95.9% and a (6S) percentage of 80.5.

One half of the mother liquor is precipitated with 1.1 g of ethanol, giving enriched amorphous (6R) tetrahydrofolic acid with a chemical content of 63.3% and a (6R) percentage of 75.9, while in the other half of the mother liquor the pH is rapidly brought to 3.5 using 6.3 g of hydrochloric acid, resulting in enriched, amorphous (6R)-tetrahydrofolic acid with a chemical content of 64.8% and a (6R) percentage of 75.9.

EXAMPLE 6

60 g of an addition salt of (6S)-tetrahydrofolic acid with benzene sulphonic acid with a (6S) percentage of 99.9, prepared as described in EP 495 204, are suspended in 240 ml of water, and the pH of the suspension is brought to 5.5 using 63 ml of 1.8 N ammonia or 55.2 ml of 2 N sodium hydroxide solution. A pH of 5.5 is maintained. The white, thick suspension is subsequently brought to pH 9.3 using 30% sodium hydroxide solution, and the resulting clear solution is heated at 50° C.

The pH is subsequently slowly brought to 5.2 using hydrochloric acid, and then, after the mixture has been seeded with crystalline (6S)-tetrahydrofolic acid, 43.0 g of crystalline (6S)-tetrahydrofolic acid with a chemical content of 96.8% and a (6S) percentage of 99.9 are obtained.

By dissolving 40 g of the resulting crystalline (6S)-tetrahydrofolic acid in 160 ml of water at pH 9 and subsequently slowly bringing the pH to 4.2, using hydrochloric acid, 32.5 g of crystalline (6S)-tetrahydrofolic acid with a chemical content of 98.5% and a (6S) percentage of 100.0 are obtained after seeding with crystalline (6S)-tetrahydrofolic acid.

Further recrystallizations at pH 4.2 give crystalline (6S)-tetrahydrofolic acid with a chemical content of >99% and a (6S) percentage of 100.0.

The solubility of the resulting crystalline (6S) tetrahydrofolic acid in water is 0.0022% at room temperature.

EXAMPLE 7

40 g of (6R,S)-tetrahydrofolic acid are suspended in 160 ml of water and 40 ml of methanol and the suspension is brought to pH 9.1 using 25% ammonia. At 50° C., the resulting solution is slowly brought to pH 5.1 using hydrochloric acid, and a pH of between 5.1 and 5.2 is maintained during the subsequent crystallization phase. When the crystallization has ended, a 20 ml sample is filtered off with suction at 50° C. and washed with water/methanol. This gives 1.3 g of crystalline (6S) tetrahydrofolic acid with a chemical content of 96.1% and a (6S) percentage of 83.0.

The main portion is cooled to 0–5° C., filtered under pressure and washed using water/methanol. This gives a further 18.6 g of crystalline (6S)-tetrahydrofolic acid with a chemical content of 90.9% and a (6S) percentage of 67.1.

EXAMPLE 8

60 g of folic acid are suspended in 240 ml of water and brought to pH 11.5 using a 30% sodium hydroxide solution. The resulting solution is reduced at 70° C. using 30 g of sodium borohydride in 120 ml of water and 12 g of 30% sodium hydroxide solution. After a reaction time of approximately 5 hours, the reaction mixture is diluted with 180 ml of water and slowly brought to pH 4.5 using hydrochloric acid. During the subsequent crystallization phase, the pH rises to approximately 5.5. The suspension is filtered under pressure at 0–5° C. and washed with a small amount of water.

This gives 25.5 g of crystalline (6S)-tetrahydrofolic acid with a chemical content of 94.4% and a (6S) percentage of 82.7. The water content after drying is 4.0%.

By dissolving 20 g of the resulting crystalline (6S)-tetrahydrofolic acid in 80 ml of water at pH 9 and subsequently slowly bringing the pH to 5.1 using hydrochloric acid, 4.5 g of crystalline (6S)-tetrahydrofolic acid with a chemical content of 94.0% and a (6S) percentage of 94.7 are obtained after seeding with crystalline (6S)-tetrahydrofolic acid. The water content after drying is 1.8%.

EXAMPLE 9

50 g of amorphous (6R)-tetrahydrofolic acid with a (6R) percentage of 99.4 are suspended in 600 ml of water and the suspension is brought to pH 9.0 using 25% ammonia. The resulting clear solution is heated at 50° C.

After subsequently slowly bringing the pH to 4.4 using hydrochloric acid and maintaining this value, 42.0 g of crystalline (6R)-tetrahydrofolic acid with a chemical content of 96.2% and a (6R) percentage of 99.5 are obtained.

The solubility of the resulting crystalline (6R)-tetrahydrofolic acid in water is 0.014% at room temperature.

Further recrystallizations at pH 4.4 give crystalline (6R)-tetrahydrofolic acid with a chemical content of >98% and a (6R) percentage of >99.5.

EXAMPLE 10

40 g of (6R,S)-tetrahydrofolic acid are suspended in 160 ml of water and the suspension is brought to pH 9.3 using 25% ammonia. At 50° C., the resulting solution is slowly brought to pH 5.1 using hydrochloric acid, and a pH of between 5.1 and 5.2 is maintained during the following crystallization phase. After crystallization has ended, the mixture is cooled to room temperature, filtered under pressure and washed with water.

18.2 g of crystalline (6S)-tetrahydrofolic acid with a chemical content of 94.0% and a (6S) percentage of 77.8 are obtained.

The mother liquor from the (6S)-tetrahydrofolic acid crystallization step is reheated to 50° C. and slowly brought to pH 4.4 using hydrochloric acid, and the pH is maintained between 4.0 and 4.5 during the subsequent crystallization of (6R)-tetrahydrofolic acid. After crystallization has ended, the mixture is cooled to room temperature, filtered under pressure and washed with water.

12 g of crystalline (6R)-tetrahydrofolic acid with a chemical content of 78.0% and a (6R) percentage of 74.8 are obtained.

EXAMPLE 11

Starting from racemic tetrahydrofolic acid, the process described was repeated at pH 5.2 and 45° C. under conditions analogous to those described in EP 600 460, Example 2. The resulting products were examined for chemical and optical purity. The chemical total yield was also recorded at each step.

|  | Percentage of 6S | Content in g/g | Purity Percentage of 6S content | Total yield |
| --- | --- | --- | --- | --- |
| Starting material | 50% | 89.6% | 44.8% | 100% |
| Run 1 | 80.5% | 96.9% | 78.0% | 53.5% |
| Run 2 | 90.0% | 97.3% | 87.6% | 45.4% |
| Run 3 | 94.4% | 97.4% | 91.9% | 42.0% |
| Run 4 | 96.4% | 96.7% | 93.2% | 38.9% |
| Run 5 | 97.7% | 96.2% | 94.0% | 35.2% |
| Run 6 | 98.4% | 95.6% | 94.1% | 32.2% |
| Run 7 | 98.9% | 96.0% | 94.9% | 28.6% |

As can be seen clearly from these data, the repeated application of this process allows the percentage of (6S) in the process product to be increased while a decrease in product content, caused by repeatedly carrying out the process, also occurs. Thus, a product with a purity of over 98% was not prepared even by repeated application of this process.

The preceding examples can be repeated with similar success by substituting the generically or specifically described reactants and/or operating conditions of this invention for those used in the preceding examples.

From the foregoing description, one skilled in the art can easily ascertain the essential characteristics of this invention, and without departing from the spirit and scope thereof, can make various changes and modifications of the invention to adapt it to various usages and conditions.

What is claimed is:

1. Crystalline (6S)-tetrahydrofolic acid having a purity by weight of more than 98%.

2. A process for the preparation of crystalline (6S)-tetrahydrofolic acid according to claim 1, comprising crystallizing (6S)- or (6R,S)-tetrahydrofolic acid in an aqueous polar medium at a pH of $\geq 3.5$, said polar medium being water or a mixture of water and a water miscible organic solvent.

3. A process according to claim 2, in which water is used as the polar medium and crystallization is effected from a solution or a suspension.

4. A process according to claim 2, wherein the pH is brought to between 3.5 and 6.5 to initiate crystallization of (6S)-tetrahydrofolic acid.

5. A process according to claim 2, characterized in that the pH is maintained constant during a crystallization step.

6. A process according to claim 2, wherein the (6R,S)-tetrahydrofolic acid is crystallized and (6S)-tetrahydrofolic acid is separated off by fractional crystallization and (6R)-tetrahydrofolic acid is isolated from the remaining mother liquor.

7. A process according to claim 2, wherein a pH of between 4.5 and 5.5 is maintained during crystallization in order to optically enrich the product.

8. A process according to claim 2, wherein a pH of between 3.5 and 4.5 is maintained during a crystallization step in order to prepared stable crystalline (6S)-tetrahydrofolic acid.

9. A compound according to claim 1, having a purity of above 99%.

10. Crystalline (6S)-tetrahydrofolic acid according to claim 1, having a content of at least 98.7% after being stored in air at 60° C. for 57 days.

11. A process for the preparation of crystalline (6S)-tetrahydrofolic acid according to claim 9, comprising crystallizing (6S)- or (6R,S)-tetrahydrofolic acid in an aqueous polar medium at a pH of $\geq 3.5$, said polar medium being water or a mixture of water and a water miscible organic solvent.

12. A process according to claim 11, wherein water is used as the polar medium and crystallization is effected from a solution or suspension.

13. A process for the preparation of crystalline (6S)-tetrahydrofolic acid according to claim 10, comprising crystallizing (6S)- or (6R,S)-tetrahydrofolic acid in an aqueous polar medium at a pH of $\geq 3.5$, said polar medium being water or a mixture of water and a water miscible organic solvent.

14. A process according to claim 13, wherein water is used as the polar medium and crystallization is effected from a solution or suspension.

15. A composition comprising a compound according to claim 1 and a pharmaceutically acceptable excipient.

16. A composition comprising a compound according to claim 9 and a pharmaceutically acceptable excipient.

17. A composition comprising a compound according to claim 10 and a pharmaceutically acceptable excipient.

* * * * *